(12) United States Patent
Lee et al.

(10) Patent No.: US 7,790,980 B2
(45) Date of Patent: Sep. 7, 2010

(54) DYE FOR DYE SENSITIZED PHOTOVOLTAIC CELL AND DYE SENSITIZED PHOTOVOLTAIC CELL PREPARED USING THE SAME

(75) Inventors: Jae-Kwan Lee, Yongin-si (KR); Ji-Won Lee, Yongin-si (KR); Wha-Sup Lee, Yongin-si (KR); Kwang-Soon Ahn, Yongin-si (KR); Jae-Man Choi, Yongin-si (KR); Moon-Sung Kang, Yongin-si (KR); Byong-Cheol Shin, Yongin-si (KR); Joung-Won Park, Yongin-si (KR); Moon-Seok Kwon, Yongin-si (KR); Soo-Jin Moon, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 1016 days.

(21) Appl. No.: 11/506,289

(22) Filed: Aug. 17, 2006

(65) Prior Publication Data

US 2007/0039644 A1   Feb. 22, 2007

(30) Foreign Application Priority Data

Aug. 18, 2005   (KR) ...................... 10-2005-0075744

(51) Int. Cl.
*H01L 31/0256* (2006.01)
*C07F 15/00* (2006.01)

(52) U.S. Cl. .......................... 136/263; 546/2; 136/252; 257/40

(58) Field of Classification Search ................. 136/263, 136/252; 257/40; 546/2
See application file for complete search history.

(56) References Cited

U.S. PATENT DOCUMENTS

| 6,278,056 B1 | 8/2001 | Sugihara et al. |
|---|---|---|
| 6,310,282 B1 | 10/2001 | Sakurai et al. |
| 6,559,375 B1 | 5/2003 | Meissner et al. |
| 6,639,073 B2 | 10/2003 | Islam et al. |
| 6,677,516 B2 | 1/2004 | Chiba et al. |

FOREIGN PATENT DOCUMENTS

| EP | 1 176 618 A1 | 1/2002 |
|---|---|---|
| EP | 1 271 581 A2 | 1/2003 |
| JP | 2002-025636 | 1/2002 |
| JP | 2002-241634 | 8/2002 |
| JP | 2006-252986 | 9/2006 |

OTHER PUBLICATIONS

Lin, R-J. et al.: Photophysics and acid-base chemistry of Re(CH3bpyCOOH)(CO)3X ( X=Cl-, and imidazole ) complexes. J. of the Chinese chem. Soc., vol. 49, pp. 161-164, 2002.*

Regan, B and Grätzel, M, *A low cost, high-efficiency solar cell based on dye-sensitized colloidal TiO₂ films*, Letters to Nature, vol. 353, Oct. 24, 1991, pp. 737-740.

Japanese Office action dated Apr. 13, 2010, for corresponding Japanese Patent application 2006- 223515, noting Japanese references in this IDS.

European Search Report dated Mar. 2, 2010, for corresponding European Patent application 06119182.1.

Nazeeruddin, K., et al., *Acid-Base Equilibria of (2,2'-Bipyridyl-4,4'-dicarboxylic acid) ruthenium (II) Complexes and the Effect of Protonation on Charge-Transfer Sensitization of Nanocrystalline Titania*, Inorganic Chemistry, vol. 38, No. 26, Jan. 1, 1999, pp. 6298-6305, XP 008050178.

Suzuki, M., et al., *Photosensitized charge separation usin ruthenium (II) complex and viologencontaining polymers—effects of quaternization and length of alkyl side-chain*, Polymer, vol. 40, No. 14, Jun. 1, 1999, pp. 3971-3978, XP004160540.

Wang, P., et al., *Amphiphilic Ruthenium Sensitizer with 4,4'-Diphosphonic Acid-2,2'-bipyridine as Anchoring Ligand for nanocrystalline Dye Sensitized Solar Cell*, Journal of Physical Chemistry, B, Materials, Surfaces, Interfaces and Biophysical, vol. 108, No. 45, Nov. 11, 2004, pp. 1755317559, XP 008068062.

* cited by examiner

*Primary Examiner*—Charanjit S Aulakh
(74) *Attorney, Agent, or Firm*—Christie, Parker & Hale, LLP (57) ABSTRACT

A dye for a dye sensitized photovoltaic cell is disclosed. A dye sensitized photovoltaic cell including the dye is also disclosed. The dye includes a metal composite treated with a cation selected from imidazolium cations, pyridinium cations, pyrrolidinium cations, and quinolidinium cations.

29 Claims, 1 Drawing Sheet

FIG.1

DYE FOR DYE SENSITIZED PHOTOVOLTAIC CELL AND DYE SENSITIZED PHOTOVOLTAIC CELL PREPARED USING THE SAME

CROSS-REFERENCE TO RELATED APPLICATION

This application claims priority to and the benefit of Korean Patent Application No. 10-2005-0075744 filed in the Korean Intellectual Property Office on Aug. 18, 2005, the entire content of which is incorporated herein by reference.

BACKGROUND OF THE INVENTION

1. Field of the Invention

The present invention relates to a dye for a dye sensitized photovoltaic cell and a dye sensitized photovoltaic cell including the same. More particularly, the present invention relates to a dye which implements an open circuit voltage, which dye includes a metal composite with an imidazolium, pyridinium, pyrrolidinium, or quinolidinium cation. The invention is also directed to a dye sensitized photovoltaic cell including such a dye and showing improved photoelectric efficiency.

2. Description of the Related Art

Diverse research has been conducted in an attempt to develop energy sources to replace conventional fossil fuels and address approaching energy crises. Particularly, extensive research is being conducted into uses for alternative energy sources (such as wind power, atomic power, and solar power) as substitutes for petroleum resources, which are expected to be used up within several decades. Among these alternative energy sources, photovoltaic cells using solar energy are available and environmentally friendly, unlike other energy sources. Since the development of Se photovoltaic cells in 1983, photovoltaic cells have drawn much attention. Recently, Si photovoltaic cells have drawn attention from researchers.

However, the practical use of Si photovoltaic cells is difficult because of high production costs and difficulties in improving cell efficiency. To address these problems, researchers have been studying and developing dye sensitized photovoltaic cells that can be produced at reduced cost.

Unlike Si photovoltaic cells, dye sensitized photovoltaic cells are electrochemical photovoltaic cells that mainly comprise photosensitive dye molecules (which absorb visible rays and produce electron-hole pairs) and transition metal oxides (which transfer the produced electrons). Among conventional dye sensitized photovoltaic cells are dye sensitized photovoltaic cells using nano titanium oxide (i.e., anatase). Dye sensitized photovoltaic cells can be produced at low cost. Also, since dye sensitized photovoltaic cells use transparent electrodes, they can be applied to external glass walls of buildings or glass greenhouses. However, dye sensitized photovoltaic cells have low photoelectric efficiency, thereby limiting their practical applications.

The photoelectric efficiency of photovoltaic cells is proportionate to the quantity of electrons produced from the absorption of solar beams. Thus, to increase the photoelectric efficiency, the quantity of electrons should be increased. Alternatively, the produced and excited electrons should not be used in electron-hole recombination. The quantity of produced electrons can be increased by raising the absorption of solar beams or the dye adsorption efficiency.

To increase the dye adsorption efficiency per unit area, nano-sized particles of oxide semiconductors have been prepared. To increase the absorption of solar beams, the reflectivity of platinum electrodes has been increased or micro-sized oxide semiconductor light scattering agents have been included. However, these conventional methods have limited impact in increasing the photoelectric efficiency of photovoltaic cells. Accordingly, a need exists for new technology capable of improving photoelectric efficiency.

The information disclosed in this Background section is presented to further the understanding of the present invention. Applicant does not admit that all information disclosed in this Background section is prior art to the present invention.

SUMMARY OF THE INVENTION

In one embodiment of the present invention, a dye for a dye sensitized photovoltaic cell has high open circuit voltage.

In another embodiment of the present invention, a dye sensitized photovoltaic cell has improved photoelectric efficiency.

According to one embodiment of the present invention, a dye for a dye sensitized photovoltaic cell includes a metal composite represented by the following Formula 1.

$$M(L_1)_{m1}(L_2)_{m2}X_{m3}Y_{m4} \quad (1)$$

In Formula 1, M is a transition element. Each of $L_1$ and $L_2$ is independently selected from ligands represented by the following Formula 1a.

(1a)

In Formula 1a, n is either 0 or 1. Each of $R_1$, $R_2$, and $R_3$ are independently selected from —$CO_2H$, —$PO_3H$, —$SO_3H$, —$CO_2^-$, —$PO_3^-$, —$SO_3^-$, C1 to C20 substituted alkyl groups, C1 to C20 unsubstituted alkyl groups, C6 to C30 substituted aryl groups, C6 to C30 unsubstituted aryl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

In Formula 1, above, X is selected from hydrogen, $NO_2$, Cl, Br, I, CN, NCS, $H_2O$, $NH_3$, Cl$^-$, Br$^-$, I$^-$, CN$^-$, NCS$^-$, and $PF_6^-$. Y is selected from imidazolium cations represented by the following Formula 1c, pyridinium cations represented by the following Formula 1d, pyrrolidinium cations represented by the following Formula 1e, and quinolidinium cations represented by the following Formula 1f.

(1c)

In the above Formulae 1c to 1f, $m_1$ is an integer ranging from 0 to 3, $m_2$ is an integer ranging from 1 to 3, $m_3$ is an integer ranging from 0 to 3, and $m_4$ is an integer ranging from 1 to 6. Each of $R_7$ through $R_{31}$ are independently selected from hydrogen atoms, hydroxy groups, C1 to C20 substituted alkyl groups, C1 to C20 unsubstituted alkyl groups, C1 to C20 substituted alkoxy groups, C1 to C20 unsubstituted alkoxy groups, C6 to C30 substituted aryl groups, C6 to C30 unsubstituted aryl groups, C1 to C20 substituted alkylthio groups, C1 to C20 unsubstituted alkylthio groups, ethers, thioethers, substituted amino groups, unsubstituted amino groups, C6 to C30 substituted aryleneoxy groups, C6 to C30 unsubstituted aryleneoxy groups, substituted alkenyl groups, unsubstituted alkenyl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

According to another embodiment of the present invention, a dye sensitized photovoltaic cell includes a first electrode, a second electrode facing the first electrode, and an electrolyte disposed between the first and second electrodes. The first electrode includes a conductive transparent substrate on a first surface and a light absorption layer on a second surface. The light absorption layer includes semiconductor particulate and a dye.

DETAILED DESCRIPTION OF THE INVENTION

The first step in the operation of a dye sensitized photovoltaic cell is the generation of a photocharge from optical energy. Generally, dye molecules are used to generate photocharges. The dye molecules are excited by absorbing light transmitted through a transparent substrate.

Among dye substances, metal composites are widely used. Specifically, the metal composites include mono ruthenium and bis or tris(substituted 2,2'-bipyridine) complex salts. However, these metal composites have low open circuit voltages, which lead to low photoelectric efficiency.

The dye sensitized photovoltaic cells of the present invention improve photoelectric efficiency by using dyes having high open circuit voltages. Specifically, a dye for a dye sensitized photovoltaic cell according to one embodiment of the present invention includes a metal composite represented by the following Formula 1.

$$M(L_1)_{m1}(L_2)_{m2}X_{m3}Y_{m4} \qquad (1)$$

In Formula 1, M is a transition element. Each of L1 and L2 is independently selected from ligands represented by the following Formula 1a.

In Formula 1a n is either 0 or 1. Each of $R_1$, $R_2$, and $R_3$ is independently selected from —$CO_2H$, —$PO_3H$, —$SO_3H$, —$CO_2^-$, —$PO_3^-$, —$SO_3^-$, C1 to C20 substituted alkyl groups, C1 to C20 unsubstituted alkyl groups, C6 to C30 substituted aryl groups, C6 to C30 unsubstituted aryl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

In Formula 1, above, X is selected from hydrogen, $NO_2$, Cl, Br, I, CN, NCS, $H_2O$, $NH_3$, Cl$^-$, Br$^-$, I$^-$, CN$^-$, NCS$^-$, and $PF_6^-$. Y is selected from imidazolium cations represented by the following Formula 1c, pyridinium cations represented by the following Formula 1d, pyrrolidinium cations represented by the following Formula 1e, and quinolidinium cations represented by the following Formula 1f.

In Formula 1c through 1f, $m_1$ is an integer ranging from 0 to 3, $m_2$ is an integer ranging from 1 to 3, $m_3$ is an integer ranging from 0 to 3, and $m_4$ is an integer ranging from 1 to 6. Each of $R_7$ through $R_{31}$ is independently selected from hydrogen, hydroxy groups, C1 to C20 substituted alkyl groups, C1 to C20 unsubstituted alkyl groups, C1 to C20 substituted alkoxy groups, C1 to C20 unsubstituted alkoxy groups, C6 to C30 substituted aryl groups, C6 to C30 unsubstituted aryl groups, C1 to C20 substituted alkylthio groups, C1 to C20 unsubstituted alkylthio groups, ethers, thioethers, substituted amino groups, unsubstituted amino groups, C6 to C30 substituted aryleneoxy groups, C6 to C30 unsubstituted aryleneoxy groups, substituted alkenyl groups, unsubstituted alkenyl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

In Formula 1, M is selected from Ru, Os, Ir, Co, Rh, Zr, Zn, and Pd. In one embodiment, M is Ru.

In the above formulae, the alkyl group is selected from C1 to C20 linear alkyl groups and C1 to C20 branched alkyl groups. In one embodiment, the alkyl group is selected from C1 to C12 linear alkyl groups and C1 to C12 branched alkyl groups. In another embodiment, the alkyl group is C1 to C6 lower alkyl group such as a methyl group, an ethyl group, a n-propyl group, an isopropyl group, a n-butyl group, an isobutyl group, a sec-butyl group, a t-butyl group, a pentyl group, an iso-amyl group, a hexyl group, and the like. In one embodiment, the alkyl group is a C1 to C3 lower alkyl radical.

In the above formulae, the alkoxy group is selected from oxygen-containing linear alkoxy groups and oxygen-containing branched alkoxy groups. In one embodiment, the alkoxy is a C1 to C20 alkoxy group. In another embodiment, the alkyl group is a C1 to C6 lower alkoxy group such as a methoxy group, an ethoxy group, a propoxy group, a butoxy group, a t-butoxy group, and the like. In yet another embodiment, the alkoxy group is a C1 to C3 lower alkoxy group.

In still another embodiment, the alkoxy group may be a haloalkoxy group in which the alkoxy group is substituted with at least one halogen atom (e.g. fluoro-substituted, chloro-substituted, or bromo-substituted). In one embodiment, the alkoxy group is a C1 to C3 haloalkoxy radical such as a fluoromethoxy group, a chloromethoxy group, a trifluoromethoxy group, a trifluoroethoxy group, a fluoroethoxy group, or a fluoropropoxy group.

In the above formulae, the aryl group may be a C6 to C30 carbocyclic aromatic based compound including at least one ring such as phenyl groups, naphthyl groups, tetrahydronaphthyl groups, indan groups, and biphenyl groups. A single aryl group may be used, or two or more aryl groups may be used in combination. The ring may be bound as a pendent group or fused. In one embodiment, the aryl group is a phenyl group.

The aryl group may have from 1 to 3 substituents such as hydroxy, halo, haloalkyl, nitro, cyano, alkoxy, and C1 to C6 lower alkylaminos.

In the above formulae, the aryloxy group may have the general formula aryl-O—, where the aryl group is as described above.

In the above formulae, the alkylthio group may have the general formula alkyl-S—, where the alkyl is as described above. In one embodiment, the alkylthio group may be a C1 to C12 linear alkyl group or a C1 to C12 branched alkyl group.

In the above formulae, the arylene group may be an aryl radical having a terminal end capable of binding, where the aryl group is as described above.

In the above formulae, the aryleneoxy group may have the general formula arylene-O—, where the arylene group may be an aryl radical having a terminal end capable of binding, where the aryl group is as described above.

In the above formulae, the alkylene group may be an alkyl radical having a terminal end capable of binding, where the alkyl is as described above.

In the above formulae, the alkyleneoxy group may have the general formula alkylene-O—, where the alkylene is as described above.

The following exemplary embodiments are presented for illustrative purposes only and are not intended to limit the scope of the present invention.

Exemplary Embodiment 1

A dye sensitized photovoltaic cell includes a dye having a metal composite represented by the above Formula 1 in which M is Ru. $L_1$ and $L_2$ in Formula 1 are each independently represented by Formula 1a above. In this embodiment, $R_1$ in Formula 1a is —$CO_2H$, $R_2$ and $R_3$ are each —$CO_2$, and n is 0. Also, in this embodiment, X in Formula 1 is NCS. In one embodiment, Y is a 1-ethyl-3-methyl imidazolium cation represented by Formula 1c above (reproduced below).

In this embodiment, $R_7$ is —$CH_2CH_3$, $R_9$ is —$CH_3$, and each of $R_8$, $R_{10}$, and $R_{11}$ is hydrogen. Also, $m_1$ is 1, $m_2$ is 1, $m_3$ is 2, and $m_4$ is 2.

Exemplary Embodiment 2

A dye sensitized photovoltaic cell includes a dye having a metal composite represented by Formula 1 in which M is Ru, and $L_1$ and $L_2$ are each independently represented by Formula 1a. Like in the previous embodiment, $R_1$ is —$CO_2H$, $R_2$ and $R_3$ are each —$CO_2$, and n is 0. Also like in the previous embodiment, X is NCS. However, in this embodiment, Y is a 1-ethyl-2,3-dimethyl imidazolium cation represented by Formula 1c above (reproduced below).

(1c)

In this embodiment, in Formula 1c $R_7$ is —$CH_2CH_3$, each of $R_8$ and $R_9$ is —$CH_3$, and each of $R_{10}$ and $R_{11}$ is hydrogen. Also, $m_1$ is 1, $m_2$ is 1, $m_3$ is 2, and $m_4$ is 2.

Exemplary Embodiment 3

A dye sensitized photovoltaic cell includes a dye having a metal composite represented by Formula 1 in which M is Ru, and $L_1$ and $L_2$ are each independently represented by Formula 1a. Like in the previous embodiments, $R_1$ is —$CO_2H$, $R_2$ and $R_3$ are each —$CO_2$, and n is 0. Also like in the previous embodiments, X is NCS. In this embodiment, however, Y is a 1-ethyl-4-tert-butyl pyridinium cation represented by Formula 1d above (reproduced below).

(1d)

In this embodiment, in Formula 1d, $R_{12}$ is —$CH_2CH_3$, $R_{15}$ is —$C(CH_3)_3$, and each of $R_{13}$, $R_{14}$, $R_{16}$, and $R_{17}$ is hydrogen. Also, $m_1$ is 1, $m_2$ is 1, $m_3$ is 2, and $m_4$ is 2.

Exemplary Embodiment 4

A dye sensitized photovoltaic cell includes a dye having a metal composite represented by Formula 1 in which M is Ru, and $L_1$ and $L_2$ are each independently represented by Formula 1a. Like in the previous embodiments, $R_1$ is —$CO_2H$, $R_2$ and $R_3$ are each —$CO_2$, and n is 0. Also like in the previous embodiments, X is NCS. However, in this embodiment, Y is a 1-butyl-4-methyl pyrrolidinium cation represented by Formula 1e above (reproduced below).

(1e)

In this embodiment, in Formula 1e, $R_{18}$ is —$CH_2CH_2CH_2CH_3$, $R_{21}$ is —$CH_3$, and each of $R_{19}$, $R_{20}$, $R_{22}$, and $R_{23}$ is hydrogen. Also, $m_1$ is 1, $m_2$ is 1, $m_3$ is 2, and $m_4$ is 2.

Exemplary Embodiment 5

A dye sensitized photovoltaic cell includes a dye having a metal composite represented by Formula 1 in which M is Ru, and $L_1$ and $L_2$ are each independently represented by Formula 1a. Like in the previous embodiments, $R_1$ is —$CO_2H$, $R_2$ and $R_3$ are each —$CO_2$, and n is 0. Also like in the previous embodiments, X is NCS. In this embodiment, however, Y is a 1-ethyl-4-methyl quinolidinium cation represented by Formula 1f above (reproduced below).

(1f)

In this embodiment, in Formula 1f, $R_{24}$ is —$CH_2CH_3$, $R_{27}$ is —$CH_3$, and each of $R_{25}$, $R_{26}$, $R_{28}$, $R_{29}$, $R_{30}$, and $R_{31}$ is hydrogen. Also, $m_1$ is 1, $m_2$ is 1, $m_3$ is 2, and $m_4$ is 2.

According to one embodiment of the present invention, a dye for a dye sensitized photovoltaic cell is applied to a light absorption layer to improve photoelectric efficiency and to increase open circuit voltage.

In another embodiment of the present invention, a dye sensitized photovoltaic cell includes an inventive dye. Specifically, the dye sensitized photovoltaic cell includes a first electrode including a conductive transparent substrate, a second electrode facing the first electrode, a light absorption layer formed on a first surface of the first electrode and positioned between the first and second electrodes, and an electrolyte positioned between the first electrode and the second electrode. The light absorption layer includes semiconductor particulate and a dye.

Figure 1:
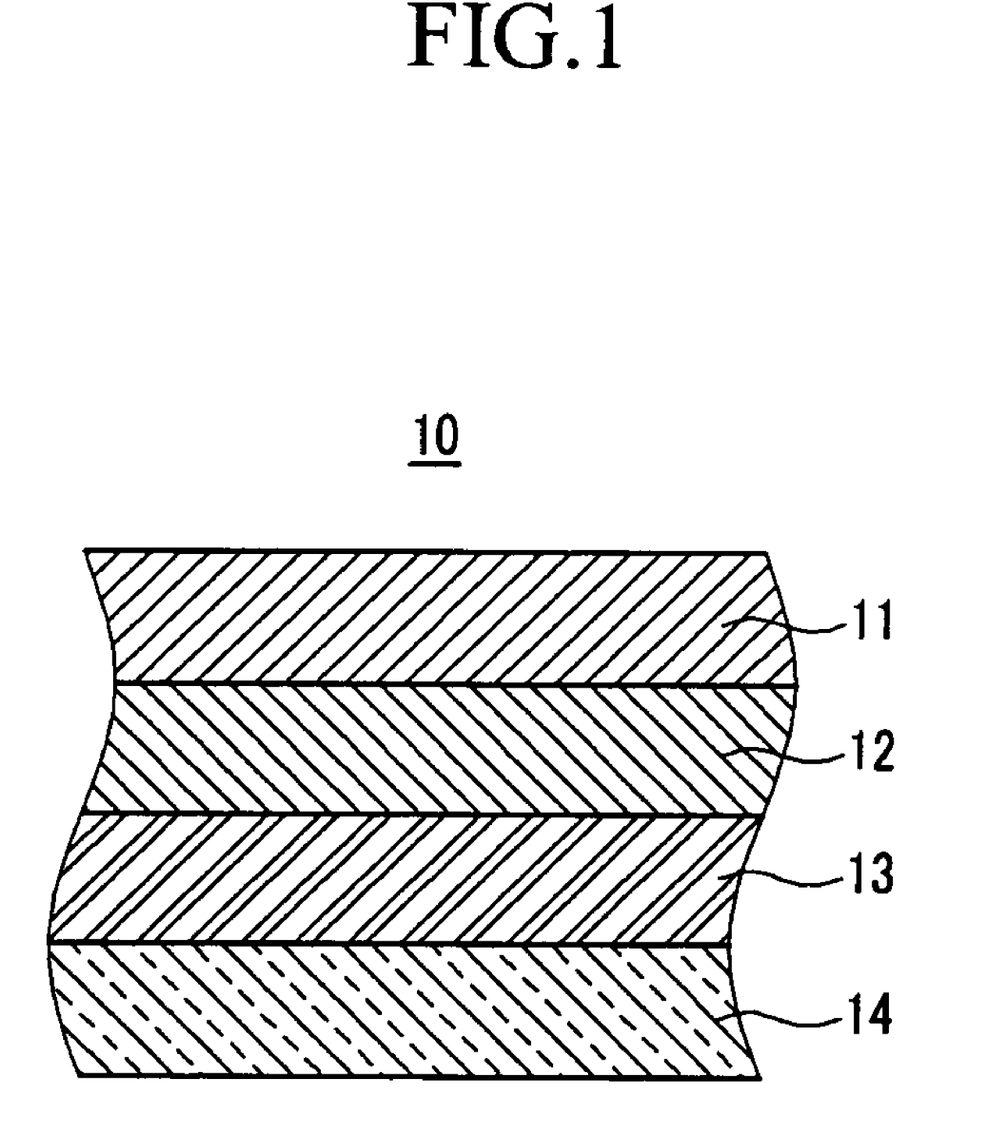
FIG. 1 is a partial cross-sectional view of a dye sensitized photovoltaic cell according to one embodiment of the present invention.

FIG. 1 is a partial cross-sectional view of a dye sensitized photovoltaic cell according to one embodiment of the present invention. As shown, the dye sensitized photovoltaic cell 10 includes two plate-type transparent electrodes, i.e. a first electrode 11 and a second electrode 14.

A first surface of the first transparent electrode 11 includes a light absorption layer 12. The light absorption layer 12 includes semiconductor particulate and a photosensitive dye adsorbed to the semiconductor particulate. The electrons of the photosensitive dye are excited by the absorption of visible rays.

The space between the first and second electrodes 11 and 14, respectively, is filled with an electrolyte 13 to facilitate oxidation-reduction reactions.

Referring to FIG. 1, the principles of operation of the dye sensitized photovoltaic cell according to one embodiment of the present invention will now be described. When solar beams enter the dye sensitized photovoltaic cell, dye molecules in the light absorption layer 12 absorb photons. The dye molecules that have absorbed the photons are excited from a ground state (which is called electron transfer) to thereby form electron-hole pairs. The excited electrons are injected into a conduction band on the semiconductor particulate interface. The injected electrons are transferred to the first electrode 11 through the interface and then transferred to the second electrode 14 (which is positioned facing the first electrode 11) through an external circuit.

The dye that is oxidized as a result of the electron transfer is reduced by ions of an oxidation-reduction couple in the electrolyte 13, and the oxidized ions are involved in a reduction reaction with electrons that have arrived at the interface of the second electrode 14 to achieve charge neutrality.

The first electrode 11 (which may be called a working electrode or a semiconductor electrode) can include any material that has conductive and transparent properties. To be specific, the first electrode 11 may be a glass substrate or a plastic substrate including at least one material selected from indium tin oxide (ITO), fluorine tin oxide (FTO), ZnO—($Ga_2O_3$ or $Al_2O_3$), and tin-based oxides. In one embodiment, the first electrode 11 may be a glass substrate including $SnO_2$ (which is conductive, transparent, and heat-resistant) and ITO (which is inexpensive).

Specific nonlimiting examples of suitable plastic substrates include polyethylene terephthalate (PET), poly(ethylene naphthalate) (PEN), polycarbonate (PC), polypropylene (PP), polyimide (PI), triacetylcellulose (TAC), and the like.

The conductive transparent substrate may be doped with a material selected from Ti, In, Ga, Al, and combinations thereof.

In one embodiment of the present invention, the light absorption layer 12 includes semiconductor particulate and an inventive dye. The dye is adsorbed to the semiconductor particulate, and the electrons of the dye are excited by the absorption of visible rays.

In one embodiment, the semiconductor particulate may be an elementary substance as the semiconductor. Nonlimiting examples of suitable semiconductor particulates include silicon, metal oxides, perovskite metal oxide composites and mixtures thereof.

The semiconductor may be an n-type semiconductor in which electrons of the conduction band become carriers through optical excitation and provide anode current.

Nonlimiting examples of suitable semiconductor particulates include Si, $TiO_2$, $SnO_2$, ZnO, $WO_3$, $Nb_2O_5$, $TiSrO_3$ and combinations thereof. In one embodiment, the semiconductor particulate is anatase ($TiO_2$).

The semiconductor particulate may have a large surface area to allow the dye adsorbed to the surface absorb much light. Specifically, the semiconductor particulate may have an average particle diameter ranging from about 15 nm to about 25 nm.

The dye is as described above.

The light absorption layer including the semiconductor particulate and the dye may be thinner than 25 μm. In one embodiment, the thickness of the light absorption layer may range from about 1 to about 25 μm.

When the light absorption layer is thicker than about 25 μm, serial resistance increases for structural reasons, and the increase in serial resistance adversely affects photoelectric efficiency. Thus, when the light absorption layer is thinner than about 25 μm, it can adequately perform its function and lower serial resistance, thereby preventing deterioration of photoelectric efficiency.

The second electrode 14 (which may be called a counter electrode) can include any material with conductive properties. The material may also be an insulating material, so long as a conductive layer is formed on a surface facing the first electrode.

Nonlimiting examples of suitable materials for the second electrode include Pt, Au, Ni, Cu, Ag, In, Ru, Pd, Rh, Ir, Os, C, conductive polymers, and combinations thereof.

The second electrode includes a substrate and a conductive layer. The substrate may be a glass substrate or a plastic substrate including at least one material selected from indium tin oxide (ITO), fluorine tin oxide (FTO), ZnO—($Ga_2O_3$ or $Al_2O_3$), a tin-based oxide, and combinations thereof. The conductive layer includes at least one material selected from Pt, Au, Ni, Cu, Ag, In, Ru, Pd, Rh, Ir, Os, C, conductive polymers, and combinations thereof.

To improve the redox catalytic effect, the surface of the second electrode facing the first electrode can have a micro structure to increase the surface area. For example, Pt or Au may be formed in a black state, and carbon may be formed as a porous structure. As used herein, 'black state' refers to a state not supported by a supporter. Particularly, platinum black may be formed by anodic oxidation onto platinum or by treating platinum with chloroplatinic acid. The porous carbon may be formed by sintering carbon particulate or by baking an organic polymer.

The electrolyte 13 comprises an electrolytic solution, and the electrolytic solution can include an iodide/triodide pair that receives and transfers electrons from the counter electrode to the dye through an oxidation-reduction reaction. The open circuit voltage is determined from the difference between the energy potential of the dye and the redox potential of the electrolyte.

The electrolytic solution is uniformly dispersed between the first and second electrodes. If the electrolytic solution is not so dispersed, it may smear into the light absorption layer.

In one nonlimiting example of a suitable electrolytic solution, the solution is prepared by dissolving iodine in acetonitrile. However, it is understood that any substance with hole conductivity can be used.

The dye sensitized photovoltaic cell having the above described structure can be prepared by first forming a first electrode having a conductive transparent substrate and forming a light absorption layer including semiconductor particulate and a dye on one surface of the first electrode. A second electrode is then formed and the first electrode having the light absorption layer is positioned facing the second electrode. The space between the first and second electrodes is then filled with an electrolyte and sealed.

Methods for preparing photovoltaic cells are known to those skilled in the art.

However, the formation of the light absorption layer will now be described in detail. First, a first electrode is prepared by coating a first surface of a conductive transparent substrate with a paste including semiconductor particulate and heat treating the substrate to thereby form a porous semiconductor particulate layer on the transparent substrate.

The properties of the paste may differ according to how the substrate is coated. Generally, the substrate is coated with the paste using a doctor blade or screen printing method. To form a transparent layer, a spin-coating or spraying method is used. Alternatively, a general wet coating method can be used.

When a binder is added to the past, the heat treatment is conducted at a temperature ranging from about 400° C. to about 600° C. for about 30 minutes. When no binder is added, the heat treatment may be conducted at a temperature lower than about 200° C.

The porosity of the porous layer may be increased and maintained by adding a polymer to the porous semiconductor particulate layer and heat treating at a temperature ranging from about 400° C. to about 600° C. The polymer should be one that does not leave organic material after heat treatment. Nonlimiting examples of suitable polymers include ethylene cellulose (EC), hydroxy propyl cellulose (HPC), polyethylene glycol (PEG), polyethylene oxide (PEO), polyvinyl alcohol (PVA), and polyvinyl pyrrolidone (PVP). Among these polymers, a polymer having an appropriate molecular weight should be used considering the coating method and coating conditions used.

Adding an appropriate polymer to the semiconductor particulate layer can improve dispersion properties and porosity. Further, the addition of the polymer increases viscosity and improves adhesion to the substrate.

The dye layer can be formed by spraying a dye solution onto the semiconductor particulate layer or by coating or impregnating the semiconductor particulate layer with the dye solution to adsorb the dye to the semiconductor particulate. The dye is naturally adsorbed to the semiconductor particulate when the first electrode having the semiconductor particulate layer is impregnated with the dye solution for about 12 hours. The dye is as described above, and the solvent dispersing the dye is not limited. Nonlimiting examples of suitable solvents include acetonitrile, dichloromethane, and alcohol-based solvents.

The dye solution in which the dye is dispersed may further include an organic pigment to improve long-wavelength visible ray absorption and to improve dye adsorption efficiency. The organic pigment may be a variety of colors. Nonlimiting examples of the organic pigment include Cumarine and pheophorbide A (which is a type of porphyrin).

After the dye layer is formed, a light absorption layer can be prepared by rinsing off the dye that is not adsorbed through solvent rinsing.

The second electrode is prepared by forming a conductive layer including a conductive substance on a conductive transparent substrate using physical vapor deposition (PVD). Nonlimiting examples of suitable PVD methods include electroplating, sputtering, and electron beam deposition.

The first electrode and the second electrode are positioned such that the light absorption layer faces the second electrode. Then, the space between the light absorption layer and the second electrode is filled with the electrolyte and sealed to prepare a dye sensitized photovoltaic cell.

The first electrode and the second electrode are positioned facing each other and sealed using an adhesive agent. The adhesive agent may be a thermoplastic polymer film such as Surlyn produced by the Dupont Company. The thermoplastic polymer film is placed between the first and second electrodes and heat and pressure are then applied to the electrodes.

An epoxy resin or an ultraviolet (UV) ray initiator may be used as the adhesive agent. The adhesive agent may be hardened after heat treatment or UV treatment.

The following examples are presented for illustrative purposes only and are not intended to limit the scope of the present invention.

EXAMPLE 1

Fabrication of a Dye Sensitized Photovoltaic Cell

A titanium oxide dispersion solution including titanium oxide particles with a particle diameter of 5 to 15 nm was applied to 1 $cm^2$ of an indium-doped tin oxide transparent conductor using a doctor blade method. The resulting product was heat treated at 450° C. for 30 minutes to form an 18 μm-thick porous titanium oxide layer.

The 18 μm-thick porous titanium oxide layer was maintained at 80° C. and impregnated with a 0.3 mM dye dispersion solution for over 12 hours to adsorb the dye. The dye dispersion solution was prepared by dissolving a metal composite according to Exemplary Embodiment 1 in ethanol.

The dye-adsorbed porous titanium oxide layer was rinsed with ethanol and dried at room temperature to thereby form a first electrode including a light absorption layer.

A second electrode was prepared by depositing a 200 nm-thick Pt layer on an indium-doped tin oxide transparent conductor by sputtering and forming micro pores with a drill having a diameter of 0.75 mm for injecting an electrolyte solution.

A 60 μm-thick thermoplastic polymer film was disposed between the first electrode and the second electrode and pressure was applied to the first and second electrodes at 100° C. for 9 seconds to adhere the two electrodes.

An oxidation-reduction electrolyte was injected through the micro pores formed in the second electrode, and the micro pores were sealed using a glass cover and a thermoplastic polymer film to thereby form a dye sensitized photovoltaic cell.

The oxidation-reduction electrolyte was prepared by dissolving 0.62 M 1,2-dimethyl-3-hexylimidazolium iodide, 0.5 M 2-aminopyrimidine, 0.1 M LiI, and 0.05 M I2 in acetonitrile solvent.

EXAMPLE 2

Fabrication of a Dye Sensitized Photovoltaic Cell

A photovoltaic cell was prepared as in Example 1, except that the 0.3 mM dye dispersion solution was prepared by dissolving a metal composite according to Exemplary Embodiment 2 in ethanol.

EXAMPLE 3

Fabrication of a Dye Sensitized Photovoltaic Cell

A photovoltaic cell was prepared as in Example 1, except that the 0.3 mM dye dispersion solution was prepared by dissolving a metal composite according to Exemplary Embodiment 3 in ethanol.

EXAMPLE 4

Fabrication of a Dye Sensitized Photovoltaic Cell

A photovoltaic cell was prepared as in Example 1, except that the 0.3 mM dye dispersion solution was prepared by dissolving a metal composite according to Exemplary Embodiment 4 in ethanol.

EXAMPLE 5

Fabrication of a Dye Sensitized Photovoltaic Cell

A photovoltaic cell was prepared as in Example 1, except that the 0.3 mM dye dispersion solution was prepared by dissolving a metal composite according to Exemplary Embodiment 5 in ethanol.

COMPARATIVE EXAMPLE 1

Fabrication of a Dye Sensitized Photovoltaic Cell

A photovoltaic cell was prepared as in Example 1, except that a 0.45 mM dye dispersion solution, prepared by dissolving $Ru(dcbpyH)_2(NCS)_2$ (dcpbyH: 2,2'-bipyridine-4,4'-carboxylic acid) in ethanol was used.

COMPARATIVE EXAMPLE 2

Fabrication of a Dye Sensitized Photovoltaic Cell

A photovoltaic cell was prepared as in Example 1, except that a 0.45 mM dye dispersion solution, prepared by dissolving $(BU_4N)_2[Ru(dcbpyH)_2(NCS)_2]$ ($BU_4N$: tetrabutylammonium cation, dcpbyH: 2,2'-bipyridine-4,4'-carboxylic acid) in ethanol was used.

Photoelectric current and voltage of the dye sensitized photovoltaic cells fabricated according to Examples 1 through 5 and Comparative Examples 1 and 2 were measured and the open circuit voltage (Voc) was calculated based on a curve of the measured photoelectric currents.

A xenon lamp (Oriel, 01193) was used as a light source, and the solar condition (AM 1.5) of the xenon lamp was corrected using a standard photovoltaic cell (Frunhofer Institute Solare Engeriessyteme, Certificate No. C-ISE369, Type of material: Mono-Si+KG filter).

The open circuit voltages (Voc) of the photovoltaic cells according to Examples 1 through 5 were 0.70V, and the open circuit voltages of the photovoltaic cells according to Comparative Examples 1 and 2 were 0.62V and 0.67V, respectively.

These results confirm that the dye sensitized photovoltaic cells including dye particles having metal composites according to the present invention produce improved open circuit voltage. The photoelectric efficiency of dye sensitized photovoltaic cells can be improved by using dyes having high open circuit voltages.

While certain embodiments of the present invention have been described for illustrative purposes, those skilled in the art will appreciate that various modifications, additions and substitutions can be made to the described embodiments without departing from the spirit and scope of invention as disclosed in the appended claims.

What is claimed is:

1. A dye for a dye sensitized photovoltaic cell, the dye comprising:
a metal composite represented by Formula 1 wherein:
M is a transition element;
each of $L_1$ and $L_2$ is independently selected from the group consisting of ligands represented by Formula 1a wherein n is an integer ranging from 0 to 1, and each of $R_1$, $R_2$, and $R_3$ is independently selected from the group consisting of —$CO_2H$, —$PO_3H$, —$SO_3H$, —$CO_2^-$, —$PO_3^-$, —$SO_3^-$, C1 to C20 substituted alkyl groups, C1 to C20 unsubstituted alkyl groups, C6 to C30 substituted aryl groups, C6 to C30 unsubstituted aryl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups;

X is selected from the group consisting of hydrogen, $NO_2$, Cl, Br, I, CN, NCS, $H_2O$, $NH_3$, Cl$^-$, Br$^-$, I$^-$, CN$^-$, NCS$^-$, and $PF_6^-$;

Y is selected from the group consisting of imidazolium cations; and each of $m_1$ and $m_3$ is an integer ranging from 0 to 3, $m_2$ is an integer ranging from 1 to 3, and $m_4$ is an integer ranging from 1 to 6.

2. The dye of claim 1, wherein Y is selected from the group consisting of imidazolium cations represented by Formula 1c:

wherein each of R7 through R11 is independently selected from the group consisting of hydrogen, hydroxy groups, C1 to C20 substituted alkyl groups, C1 to C20 unsubstituted alkyl groups, C1 to C20 substituted alkoxy groups, C1 to C20 unsubstituted alkoxy groups, C6 to C30 substituted aryl groups, C6 to C30 unsubstituted aryl groups, C1 to C20 substituted alkylthio groups, C1 to C20 unsubstituted alkylthio groups, ethers, thioethers, substituted amino groups, unsubstituted amino groups, C6 to C30 substituted aryleneoxy groups, C6 to C30 unsubstituted aryleneoxy groups, substituted alkenyl groups, unsubstituted alkenyl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

3. The dye of claim 1, wherein M is selected from the group consisting of Ru, Os, Ir, Co, Rh, Zr, Zn, Pd, and combinations thereof.

4. The dye of claim 1, wherein the alkyl group is selected from the group consisting of C1 to C20 linear alkyl groups and C1 to C20 branched alkyl groups.

5. The dye of claim 2, wherein the alkyl group is selected from the group consisting of C1 to C20 linear alkyl groups and C1 to C20 branched alkyl groups.

6. The dye of claim 2, wherein the alkoxy group is selected from the group consisting of C1 to C6 lower alkoxy groups.

7. The dye of claim 2, wherein the alkoxy is substituted with at least one halogen atom.

8. The dye of claim 1, wherein the aryl group has from 1 to 3 substituents, each substituent being selected from the group consisting of hydroxy, halo, haloalkyl, nitro, cyano, alkoxy, and C1 to C6 lower alkylaminos.

9. The dye of claim 2, wherein the aryl group comprises from 1 to 3 substituents, each substituent being selected from the group consisting of hydroxy, halo, haloalkyl, nitro, cyano, alkoxy, and C1 to C6 lower alkylaminos.

10. The dye of claim 2, wherein the alkylthio group is represented by alkyl-S—, wherein the alkyl is selected from the group consisting of C1 to C12 linear alkyl groups and C1 to C12 branched alkyl groups.

11. The dye of claim 1, wherein:
M is Ru;
each of $L_1$ and L2 is selected from the group consisting of ligands represented by Formula 1a

(1a)

wherein $R_1$ is —$CO_2H$, each of $R_2$ and $R_3$ is —$CO_2^-$, and n is 0;
X is NCS;
$m_1$ is 1, $m_2$ is 1, $m_3$ is 2, and $m_4$ is 2; and
Y is selected from the group consisting of 1-ethyl-3-methyl imidazolium cations, and 1-ethyl-2,3-dimethyl imidazolium cations.

12. A dye sensitized photovoltaic cell comprising:
a first electrode comprising a conductive transparent substrate;
a light absorption layer disposed on a first surface of the first electrode, the light absorption layer comprising semiconductor particulate and a dye, the dye comprising a metal composite represented by Formula 1

$$M(L_1)_{m1}(L_2)_{m2}X_{m3}Y_{m4} \quad (1)$$

wherein:
M is a transition element;
each of $L_1$ and $L_2$ is independently selected from the group consisting of ligands represented by Formula 1a, (1a)

wherein n is an integer ranging from 0 to 1 and each of $R_1$, $R_2$, and $R_3$ is independently selected from the group consisting of —$CO_2H$, —$PO_3H$, —$SO_3H$, —$CO_2^-$, —$PO_3^-$, —$SO_3^-$, C1 to C20 substituted alkyl groups, C1 to C20 unsubstituted alkyl groups, C6 to C30 substituted aryl groups, C6 to C30 unsubstituted aryl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups and C1 to C20 unsubstituted alkyleneoxy groups;

X is selected from the group consisting of hydrogen, $NO_2$, Cl, Br, I, CN, NCS, $H_2O$, $NH_3$, $Cl^-$, $Br^-$, $I^-$, $CN^{31}$, $NCS^-$, and $PF_6^-$;
Y is selected from the group consisting of imidazolium cations; and
each of $m_1$ and $m_3$ is an integer ranging from 0 to 3, $m_2$ is an integer ranging from 1 to 3; and $m_4$ is an integer ranging from 1 to 6;
a second electrode facing the first electrode; and
an electrolyte disposed between the first electrode and the second electrode.

13. The dye sensitized photovoltaic cell of claim 12, wherein Y is selected from the group consisting of imidazolium cations represented by Formula 1c:

(1c)

wherein each of R7 through R11 is independently selected from the group consisting of hydrogen, hydroxy groups, C1 to C20 substituted alkyl groups, C1 to C20 unsubstituted alkyl groups, C1 to C20 substituted alkoxy groups, C1 to C20 unsubstituted alkoxy groups, C6 to C30 substituted aryl groups, C6 to C30 unsubstituted aryl groups, C1 to C20 substituted alkylthio groups, C1 to C20 unsubstituted alkylthio groups, ethers, thioethers, substituted amino groups, unsubstituted amino groups, C6 to C30 substituted aryleneoxy groups, C6 to C30 unsubstituted aryleneoxy groups, substituted alkenyl groups, unsubstituted alkenyl groups, C6 to C30 substituted aryloxy groups, C6 to C30 unsubstituted aryloxy groups, C6 to C30 substituted arylene groups, C6 to C30 unsubstituted arylene groups, C1 to C20 substituted alkylene groups, C1 to C20 unsubstituted alkylene groups, C1 to C20 substituted alkyleneoxy groups, and C1 to C20 unsubstituted alkyleneoxy groups.

14. The dye sensitized photovoltaic cell of claim 12, wherein M is selected from the group consisting of Ru, Os, Ir, Co, Rh, Zr, Zn, Pd, and combinations thereof.

15. The dye sensitized photovoltaic cell of claim 12, wherein the alkyl group is selected from the group consisting of C1 to C20 linear alkyl groups and C1 to C20 branched alkyl groups.

16. The dye sensitized photovoltaic cell of claim 13, wherein the alkyl group is selected from the group consisting of C1 to C20 linear alkyl groups and C1 to C20 branched alkyl groups.

17. The dye sensitized photovoltaic cell of claim 13, wherein the alkoxy group is selected from the group consisting of C1 to C6 lower alkoxy groups.

18. The dye sensitized photovoltaic cell of claim 13, wherein the alkoxy is substituted with at least one halogen atom.

19. The dye sensitized photovoltaic cell of claim 12, wherein the aryl group has from 1 to 3 substituents, each substituent being selected from the group consisting of hydroxy, halo, haloalkyl, nitro, cyano, alkoxy, and C1 to C6 lower alkylaminos.

20. The dye sensitized photovoltaic cell of claim 13, wherein the aryl group comprises from 1 to 3 substituents, each substituent being selected from the group consisting of hydroxy, halo, haloalkyl, nitro, cyano, alkoxy, and C1 to C6 lower alkylaminos.

21. The dye sensitized photovoltaic cell of claim 13, wherein the alkylthio group is represented by alkyl-S—, wherein the alkyl is selected from the group consisting of C1 to C12 linear alkyl groups and C1 to C12 branched alkyl groups.

22. The dye sensitized photovoltaic cell of claim 12, wherein:

M is Ru;

each of $L_1$ and L2 is selected from the group consisting of ligands represented by Formula 1a (1a)

wherein $R_1$ is —$CO_2H$, each of $R_2$ and $R_3$ is —$CO_2^-$, and n is 0;

X is NCS;

$m_1$ is 1, $m_2$ is 1, $m_3$ is 2, and $m_4$ is 2; and

Y is selected from the group consisting of 1-ethyl-3-methyl imidazolium cations, and 1-ethyl-2,3-dimethyl imidazolium cations.

23. The dye sensitized photovoltaic cell of claim 12, wherein the conductive transparent substrate is selected from the group consisting of glass substrates and plastic substrates comprising a material selected from the group consisting of indium tin oxide, fluorine tin oxide, ZnO—$Ga_2O_3$, ZnO—$Al_2O_3$, a tin-based oxide, and combinations thereof.

24. The dye sensitized photovoltaic cell of claim 12, wherein the conductive transparent substrate comprises a plastic substrate selected from the group consisting of polyethylene terephthalate, polyethylenenaphthalate, polycarbonate, polypropylene, polyimide, triacetylcellulose, and combinations thereof.

25. The dye sensitized photovoltaic cell of claim 12, wherein the semiconductor particulate is selected from the group consisting of elementary substances, metal oxides, perovskite composite metal oxides, and combinations thereof.

26. The dye sensitized photovoltaic cell of claim 12, wherein the semiconductor particulate is selected from the group consisting of $TiO_2$, $SnO_2$, ZnO, $WO_3$, $Nb_2O_5$, $TiSrO_3$, and combinations thereof.

27. The dye sensitized photovoltaic cell of claim 12, wherein the semiconductor particulate has an average particle diameter of about 50 nm or less.

28. The dye sensitized photovoltaic cell of claim 12, wherein the light absorption layer has a thickness of about 25 µm or less.

29. The dye sensitized photovoltaic cell of claim 12, wherein the second electrode comprises a material selected from the group consisting of Pt, Au, Ni, Cu, Ag, In, Ru, Pd, Rh, Ir, Os, C, conductive polymers, and combinations thereof.

* * * * *

UNITED STATES PATENT AND TRADEMARK OFFICE
CERTIFICATE OF CORRECTION

PATENT NO. : 7,790,980 B2  Page 1 of 1
APPLICATION NO. : 11/506289
DATED : September 7, 2010
INVENTOR(S) : Jae-Kwan Lee et al.

It is certified that error appears in the above-identified patent and that said Letters Patent is hereby corrected as shown below:

On the Title Page (56) References  Delete "viologencontaining"
OTHER PUBLICATIONS, line 18  Insert --viologen-containing--

(56) References  Delete "1755317559"
OTHER PUBLICATIONS, line 25  Insert --17553-17559--

In the Claims

Column 16, Claim 12, line 3  Delete "$CN^{31}$"

Insert --$CN^-$--

Signed and Sealed this
Tenth Day of January, 2012

David J. Kappos
*Director of the United States Patent and Trademark Office*